United States Patent

Marion et al.

[11] Patent Number: 6,159,344
[45] Date of Patent: Dec. 12, 2000

[54] REACTION AND DISTILLATION DEVICE

[75] Inventors: Marie-Claire Marion, Villeurbanne; Alain Forestiere, Vernaison, both of France; Christophe Thille, Charleroi, Belgium; Jean-Charles Viltard, Valence, France

[73] Assignee: Institut Francais du Petrole, Cedex, France

[21] Appl. No.: 08/900,878

[22] Filed: Jul. 25, 1997

[30] Foreign Application Priority Data

Jul. 26, 1996 [FR] France ..................... 96 09553

[51] Int. Cl.$^7$ .................. B01D 3/00; C07C 41/42
[52] U.S. Cl. .................. 202/154; 202/155; 202/158; 202/160; 202/161; 202/172; 203/2; 203/29; 203/75; 203/99; 203/DIG. 6; 203/DIG. 19; 422/190; 422/212; 422/261; 568/697; 568/699
[58] Field of Search ................ 203/29, 2, DIG. 6, 203/71–75, 78, 80, 99, 77, DIG. 19; 202/158, 153, 154, 155, 160, 161, 172; 568/697, 699; 422/190, 212, 236, 234, 261

[56] References Cited

U.S. PATENT DOCUMENTS

| | | | |
|---|---|---|---|
| 4,503,265 | 3/1985 | Schleppinghoff et al. | 568/697 |
| 4,849,569 | 7/1989 | Smith, Jr. | 568/793 |
| 5,013,407 | 5/1991 | Nocca et al. | 202/158 |
| 5,091,590 | 2/1992 | Harandi et al. | 568/697 |
| 5,132,467 | 7/1992 | Haag et al. | 568/697 |
| 5,215,725 | 6/1993 | Sy | 422/212 |
| 5,231,234 | 7/1993 | Arganbright et al. | 568/697 |
| 5,364,975 | 11/1994 | Nocca et al. | 568/697 |
| 5,368,691 | 11/1994 | Asselineau et al. | 203/29 |
| 5,420,360 | 5/1995 | Chin et al. | 568/697 |
| 5,493,059 | 2/1996 | Sanfilippo et al. | 568/697 |
| 5,628,880 | 5/1997 | Hearn et al. | 203/DIG. 6 |
| 5,637,777 | 6/1997 | Aittamaa et al. | 203/29 |

FOREIGN PATENT DOCUMENTS

| | | |
|---|---|---|
| 0 537 636 | 4/1993 | European Pat. Off. |
| 93/20032 | 10/1993 | WIPO . |

*Primary Examiner*—Virginia Manoharan
*Attorney, Agent, or Firm*—Millen, White, Zelano & Branigan

[57] ABSTRACT

The invention relates to a distillation and reaction device having a reaction section and a distillation-reaction section. The distillation-reaction section has a distillation zone with at least one device for circulation of the effluent from the reaction section to the distillation zone. Effluent from the reaction section is circulated to the distillation zone. The distillation-reaction section also has at least one distillation-reaction zone having at least one catalyst bed. The distillation-reaction zone is distinct from the distillation zone and provides at least partly the reflux of the distillation zone. The distillation-reaction section can also have at least one complementary reaction zone containing at least one catalyst bed. The invention further relates to a process for preparing at least one aliphatic monoalcohol, generally in excess, and at least one olefin.

24 Claims, 8 Drawing Sheets

REACTION AND DISTILLATION DEVICE

FIELD OF THE INVENTION

The present invention relates to a reaction and distillation device and to a process for preparing a tertiary alkyl ether by reaction of at least one olefin with an aliphatic monoalcohol, generally in excess.

BACKGROUND OF THE INVENTION

It is well-known to prepare tertiary alkyl ethers by reacting an iso-olefin generally contained in a hydrocarbon fraction with an aliphatic alcohol, generally used in excess, in the presence of an acid catalyst, for example sulfuric acid, hydrofluoric acid, aluminium chloride or boron fluoride, or int he presence of carbonaceous matter containing sulfonic groups (—SO3H), for example sulfonated coal, sulfonated phenol-formaldehyde resins, sulfonated coumarone-indene polymers or preferably sulfonated styrene-divinylbenzene copolymer resins or other compounds, notably mineral compounds, comprising sulfonic groups (for example sulfonated polysiloxanes).

It has been known for a long time that the reaction between an aliphatic monoalcohol and a tertiary olefin is balanced and that it is difficult to obtain iso-olefin conversion coefficients with a high purity and yield. Conventional processes such as those described for example in Hydrocarbon Technology International, Autumn 95, p. 21–27, comprise one or more reactor(s) for etherification to tertiary alkyl ethers followed by at least one fractionating zone, generally a distillation zone, whose bottom product is ether containing the lowest possible amount of monoalcohol(s).

This is the reason why the prior art recommended, in order to improve the performances of this synthesis, to add a complementary reaction section to the main reactor, as described for example in U.S. Pat. No. 5,364,975 in the name of the applicant. In this patent, the complementary reaction section is included, according to a preferred embodiment, in the reflux device of the fractionating section. It has also been proposed, for example in U.S. Pat. No. 4,503,265 or in patent applications WO-A-93/19,031 and WO-A-93/19,032, to draw off a product from an intermediate tray of the fractionating section, to feed this product into a complementary reaction section and to feed the product from this complementary reaction section back into the fractionating section at a level below the draw-off level. The drawback of this embodiment is that it disrupts the smooth running of the distillation process in the fractionating section. A process of the UOP Company known as Ethermax, wherein the effluent from the main etherification section is fed into a distillation-reaction zone, has also been described for example in Hydrocarbon Processing, March 1995, p. 114. As shown hereafter in a comparative example, this process has the drawback of requiring a column of very great height to obtain a very appreciable improvement of the global performances. These conventional processes for preparing tertiary alkyl ethers will be described hereafter in connection with FIGS. 1, 2 and 3.

One of the objects of the invention is to overcome the main drawbacks of the processes described in the prior art and to propose several ether synthesis embodiments allowing to maximize global conversion of the iso-olefins contained in hydrocarbon cuts.

The feed consisting of a mixture of C4, C5, C6 or C7 hydrocarbons comprising iso-olefins and at least one aliphatic monoalcohol generally used in excess is fed into the main reaction section represented by reactor R1 in FIGS. 1 to 9. The mixed reactants are brought into contact with an acid catalyst.

Figure 1:
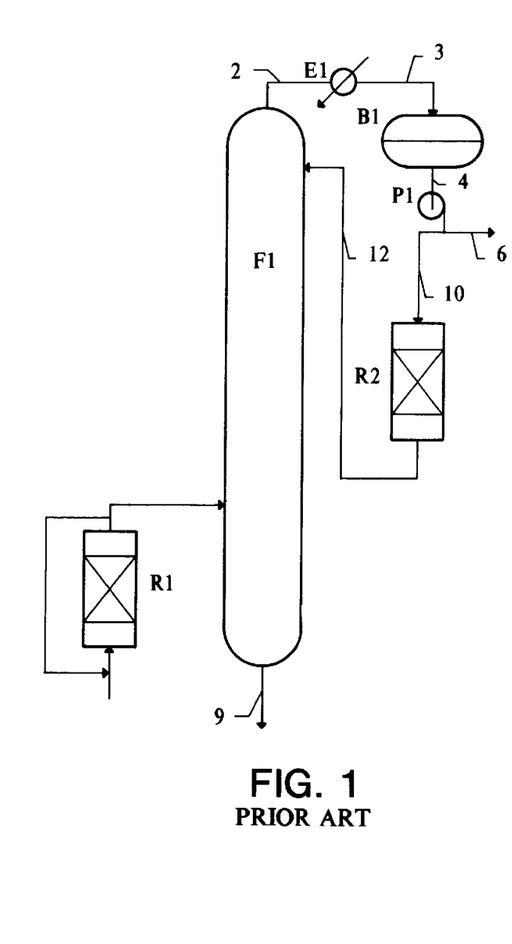
FIG. 1 illustrates an embodiment according to U.S. Pat. No. 5,364,975.
Figure 2:
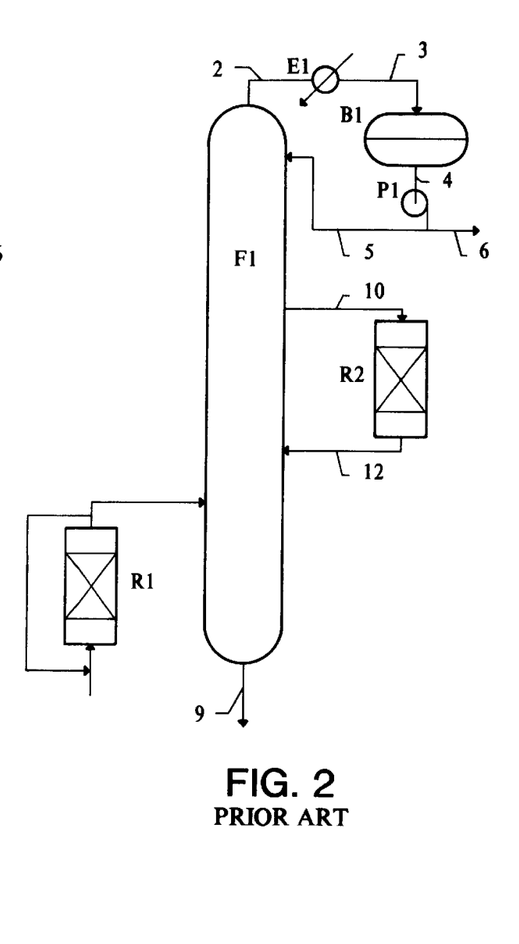
FIG. 2 illustrates an embodiment according to U.S. Pat. No. 4,503,265.
Figure 3:
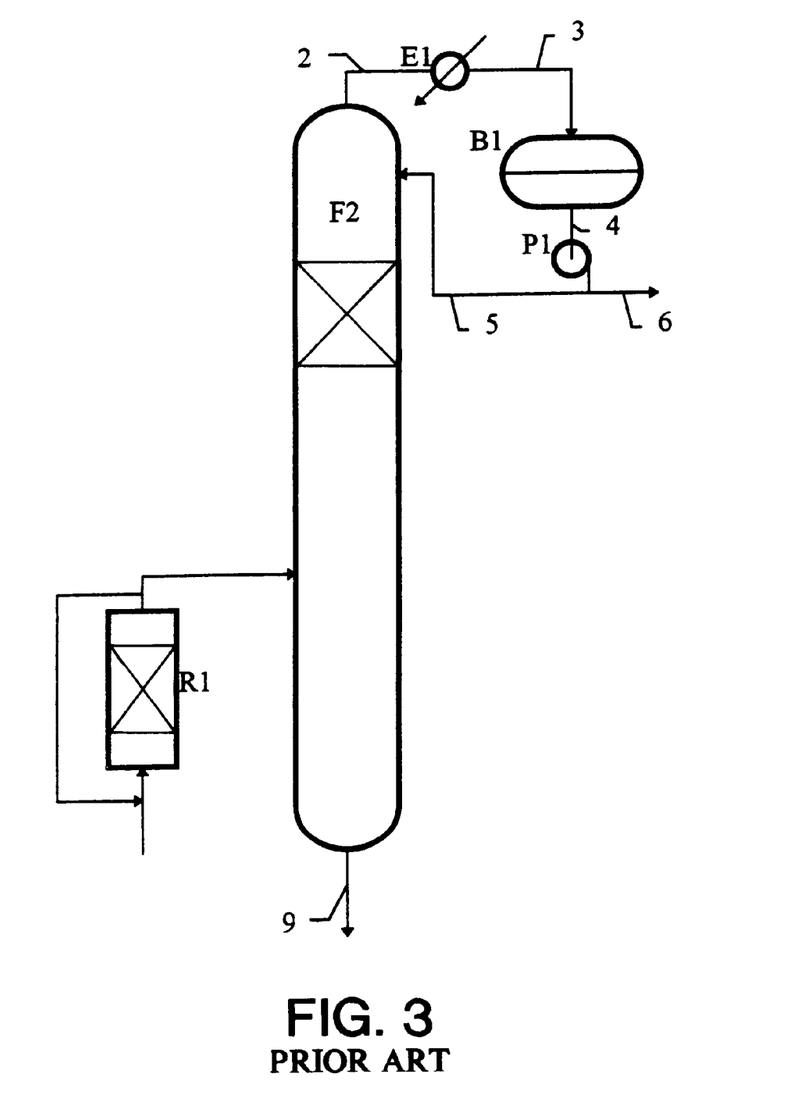
FIG. 3 illustrates an embodiment according to Hydrocarbon Processing, March 1995, page 114.

The product from this reaction section R1 is fed into a distillation zone represented by column F1 in FIGS. 1 and 2 and by column F2 in FIG. 3. It is distilled in this column in order to produce, at the bottom, through line 9, a tertiary alkyl ether containing the lowest possible amount of monoalcohol(s), and at the top, through line 2, a mixture of reactive and non reactive hydrocarbons and of aliphatic monoalcohol(s) carried over by azeotropy. This effluent flowing out through line 2 is condensed in condenser E1 and collected through line 3 in drum B1 prior to flowing into pump P1 through line 4.

In the instance schematized in FIG. 1 (U.S. Pat. No. 5,364,975), part of the effluent leaving pump P1 is fed through line 10 into a reactor R2 referred to as finishing reactor, whose effluent is fed through line 12 into column F1 as reflux and the rest of the effluent flows off as distillate through line 6.

In the embodiment schematized in FIG. 2 (U.S. Pat. No. 4,503,265), a product is drawn off from an intermediate tray of the distillation column between the effluent introduction point of etherification reactor R1 and the top of this column, and this product is fed through line 10 into a reactor R2 referred to as finishing reactor, whose effluent is fed through line 12 into column F1 at a level below the level of the draw-off point. In the instance schematized in FIG. 2, part of the effluent flowing out of pump P1 is fed through line 5 into column F1 as reflux and the rest of the effluent flows off as distillate through line 6.

In the embodiment schematized in FIG. 3 (Hydrocarbon Processing, March 1995, p. 114), the effluent of the reaction section R1 is fed into a distillation-reaction column beneath the first catalyst bed and part of the effluent flowing out of pump P1 is fed through line 5 into column F1 as reflux and the rest of the effluent flows off as distillate through line 6.

However, such a process requires in the instance schematized in FIG. 3 a great number of reaction zones in distillation-reaction column F2 in order to obtain high conversions into iso-olefins and consequently a column of great height. In fact, obtaining high conversions requires a distillation-reaction column containing many reaction zones. Insofar as one of these zones alone occupies about 3 meters in height in the distillation-reaction column, the final height of this column quickly becomes limitative. It would therefore be interesting to have such a high conversion to iso-olefins while keeping a limited number of reaction zones in the column and/or to limit the height of the column. This is one of the objectives of the invention as described hereafter in connection with FIGS. 4, 5, 6, 7, 8 and 9.

DESCRIPTION OF THE INVENTION

The present invention thus relates to a distillation and reaction device comprising:
 a) a reaction section,
 b) a distillation-reaction section comprising a distillation zone, comprising at least one means intended for circulation of the effluent from the reaction section to said distillation zone, and at least one distillation-reaction zone, comprising at least one catalyst bed, said distillation-reaction zone being distinct from the distillation zone and providing at least partly, preferably for the most part, most preferably practically entirely the reflux of the distillation zone.

The device according to the invention preferably comprises at least one means intended for circulation of the effluent between the top of the distillation zone and the bottom of the distillation-reaction zone and at least one means intended for circulation of the effluent between the bottom of the distillation-reaction zone and the top of the distillation zone.

The device according to the invention preferably also comprises at least one means for feeding the reaction section and at least one means for drawing off product at the bottom of the distillation zone.

According to one of the embodiments of the invention, independent or not of the previous embodiments, the device according to the invention is such that the distillation-reaction zone comprises at least one reflux device, which generally comprises at least one draw-off means situated at the top of the distillation-reaction zone, feeding at least one condensation zone, at least one means intended for circulation of part of the effluent from said condensation zone towards the top of the distillation-reaction zone and at least one means for drawing off (generally outside the distillation-reaction section) another part of the effluent from the condensation zone.

A preferred implementation of the device according to the invention is preferably such that said device is characterized in that said distillation-reaction section comprises at least one complementary reaction section, comprising at least one catalyst bed. Such a preferred implementation comprises three embodiments which are described hereafter, and said embodiments can be combined with one another for said preferred implementation of the device according to the invention.

According to a first preferred embodiment according to the invention, within the scope of said implementation, the device is such that the complementary reaction section is connected on the one hand to said distillation zone, at the height of a draw-off level, by a feed means, and connected on the other hand to said distillation zone in proximity to, generally substantially below, said level by a means intended for circulation of the effluent of said complementary reaction section. In said first embodiment, the draw-off level is preferably situated between the feed point of the distillation zone and the top of said distillation zone.

According to a second preferred embodiment according to the invention, within the scope of said implementation, the device is such that the complementary reaction section is connected on the one hand to said distillation-reaction zone, at the height of a draw-off level, by a feed means, and connected on the other hand to said distillation-reaction zone in proximity to, generally substantially below, said level by a means intended for circulation of the effluent of said complementary reaction section. In said second embodiment, the draw-off level is preferably situated between the bottom of the distillation-reaction zone and the bottom of the catalyst bed situated in the lowest part of said distillation-reaction zone.

According to a third preferred embodiment according to the invention, within the scope of said implementation, the device is such that the complementary reaction section is situated at least partly on the means intended for circulation (as reflux) of the effluent from the distillation-reaction zone to the distillation zone, i.e. the means intended for circulation of the effluent from the distillation-reaction zone to the distillation zone, one end of which is generally situated at the bottom of the distillation-reaction zone, is connected to the complementary reaction section, and the means intended for circulation of the effluent from the complementary reaction section to the distillation zone provides at least partly the reflux of the distillation zone. There is possibly another means for circulating the effluent directly between the bottom of the distillation-reaction zone and the top of the distillation zone, providing at least another part of the reflux.

Generally, within the scope of said preferred implementation, whatever the embodiment of the device according to the invention, the means for feeding the complementary reaction section preferably comprises at least one temperature control means allowing to adjust the temperature of the effluent flowing into the complementary reaction section, usually in order to obtain the maximum conversion in said complementary reaction section.

Similarly, within the scope of said preferred implementation, whatever the embodiment of the device according to the invention, the means intended for circulation of the effluent of the complementary reaction section preferably comprises at least one temperature control means allowing to adjust the temperature of the effluent flowing out of the complementary reaction section, usually in order to recover the thermal level of the zone into which the major part of said effluent flows thereafter.

Besides, within the scope of said preferred implementation, whatever the embodiment of the device according to the invention, the complementary reaction section comprises at least one additional reactant delivery means, usually in order to adjust the conversion in said complementary reaction section.

The invention also relates to a process for preparing at least one tertiary alkyl ether by reaction of at least one aliphatic monoalcohol with at least one olefin, comprising:

a) contacting in a reaction section at least one olefin and at least one aliphatic alcohol, generally in excess, b) introducing, through at least one circulation means, the major part of the effluent of said reaction section into a distillation-reaction section comprising a distillation zone and at least one distillation-reaction zone, comprising at least one catalyst bed, said distillation-reaction zone being distinct from the distillation zone and providing at least partly, preferably for the most part, most preferably practically entirely, the reflux of the distillation zone, c) drawing off, at the bottom of the distillation zone, tertiary alkyl ether and at the top of the distillation-reaction zone, an effluent comprising unreacted hydrocarbons and residual aliphatic alcohol.

The process according to the invention is preferably such that the major part of an effluent drawn off at the top of the distillation zone is fed into the distillation-reaction zone and the major part of an effluent that is recovered at the bottom of the distillation-reaction zone is fed to the top of the distillation zone.

The process according to the invention is also preferably such that the reflux of the distillation-reaction zone is provided by drawing off, at the top of the distillation-reaction zone, at least one effluent the major part of which is condensed, part of said condensed effluent being re-introduced at the top of the distillation-reaction zone and the other part of said condensed effluent forming mainly the part drawn off as described at c) above.

A preferred implementation of the process according to the invention is preferably such that said process is characterized in that said distillation-reaction section comprises at least one complementary reaction section, comprising at least one catalyst bed.

Such a preferred implementation comprises three embodiments which are described hereafter, and said embodiments can be combined with each other in order to achieve said preferred implementation of the process according to the invention.

According to a first preferred embodiment according to the invention, within the scope of said preferred implementation, the process is such that the complementary reaction section is supplied with at least part, preferably with the most part of an effluent drawn off at the height of a draw-off level of the distillation zone, the effluent of said complementary reaction section being fed for the most part into said distillation zone in proximity to, generally substantially below said level. In said first embodiment, the effluent is preferably drawn off between the feed point of the distillation zone and the top of said distillation zone.

According to a second preferred embodiment according to the invention, within the scope of said preferred implementation, the process is such that the complementary reaction section is fed with at least part, preferably with the most part of an effluent drawn off at the height of a draw-off level of the distillation-reaction zone, the effluent of said complementary reaction section being fed back into said distillation-reaction zone in proximity to, generally substantially below said level. In said second embodiment, the effluent is preferably drawn off between the bottom of the distillation-reaction zone and the bottom of the catalyst bed situated in the lowest part of said distillation-reaction zone.

According to a third preferred embodiment according to the invention, within the scope of said preferred implementation, the process is such that at least part, preferably the most part of the effluent circulating from the distillation-reaction zone to the distillation zone in order to provide at least partly the reflux of the distillation zone, passes through the complementary reaction section, i.e. at least part, preferably the most part of said effluent is fed into the complementary reaction section, then the major part of the effluent of said complementary reaction section is fed into the distillation zone. Another part of the effluent possibly circulates directly from the distillation-reaction zone to the distillation zone.

Generally, within the scope of said preferred implementation, whatever the embodiment of the device according to the invention, the temperature of the effluent flowing into the complementary reaction section is preferably controlled, which allows to adjust the temperature of the effluent flowing from the complementary reaction section, usually in order to obtain the maximum conversion in said complementary reaction section.

Similarly, within the scope of said preferred implementation, whatever the embodiment of the device according to the invention, the temperature of the effluent flowing from the complementary reaction section and flowing into the distillation zone is preferably controlled, which allows to adjust the temperature of the effluent flowing into the complementary reaction section, usually in order to recover the thermal level of the zone into which the most part of said effluent flows thereafter.

Besides, within the scope of said preferred implementation, whatever the embodiment of the device according to the invention, the complementary reaction section is preferably supplied with additional aliphatic alcohol, which usually allows to optimize the ether(s) yield in said complementary reaction section.

Finally, in the etherification process, the presence of the complementary reaction section, when there is one, advantageously allows to control at best two significant parameters which are the temperature and the addition of alcohol to said section, which favours optimization of the ether(s) conversion or yield.

The device according to the invention as shown in FIGS. 4, 5, 6, 7, 8 and 9 comprises a fractionating column F1. The effluent at the bottom of distillation-reaction column F2 is used as the reflux of fractionating column F1, in which case, (1) in the presence of finishing reactor R2, said reactor is fed by drawing off liquid from a draw-off level of distillation-reaction column F2, the effluent of said reactor R2 being then re-injected slightly below said level in column F2 (see FIG. 8); or (2) the effluent at the bottom of distillation-reaction column F2 is used as feed of finishing reactor R2 whose product is thereafter used as reflux of fractionating column F1; or said reactor is fed by drawing off liquid from distillation column F1, the effluent of said reactor R2 being then re-injected slightly below said level into column F1 (see FIG. 4).

The process according to the invention is more particularly a process for preparing tertiary alkyl ether from isobutene and ethanol or other aliphatic monoalcohols such as methanol, propanol or isopropanol, and for preparing other tertiary alkyl ethers from C4, C5, C6 and C7 iso-olefins and C1 to C4 aliphatic monoalcohols, in particular methanol, propanol and isopropanol. It thus relates more particularly to the preparation of methyl tert-butyl ether (MTBE), ethyl tert-butyl ether (ETBE) and tert-amyl methy ether (TAME). In all cases, the alcohol(s) is (are) generally in excess in relation to the olefin(s).

The feed used to prepare the tertiary alkyl ether according to the process of the invention generally contains at least one iso-olefin capable of reacting with the aliphatic monoalcohol in the etherification reaction giving rise to tertiary alkyl ether.

Most often, but this is not essential, the feeds processed are cuts resulting from catalytic cracking and steam cracking after fractionation. According to fractionation, these feeds can contain small proportions of hydrocarbons whose number of carbon atoms per molecule is less or greater than that of the iso-olefins to be processed.

After reaction in reaction section R1, conducted under conventional conditions (generally under the following operating conditions: in the liquid or mixed phase, at a pressure of 0.2 to 3 MPa, preferably 0.5 to 2 MPa, at a temperature between 30 and 150° C., preferably between 40 and 100° C.), the effluent flowing from reactor R1 generally contains tertiary alkyl ether, the non-reactive hydrocarbons contained in the feed, the non-converted hydrocarbons and the excess aliphatic monoalcohol. This effluent is fed into the fractionating section where it is distilled, generally under an absolute pressure of 0.3 to 1 MPa and at a bottom temperature of 80 to 160° C.

The top effluent flowing from fractionating section F1 through line 1 contains the non-reactive hydrocarbons of the feed, the non-converted hydrocarbons and the excess aliphatic monoalcohol. This effluent is thereafter injected into distillation-reaction column F2. The bottom product of this distillation-reaction column is used as reflux of fractionating column F1 and comprises non-reactive hydrocarbons, hydrocarbons that have not been converted in the first reaction section R1, the excess aliphatic monoalcohol and ether. The bottom effluent leaving distillation-reaction section F2 through line 7 contains the non-reactive hydrocarbons of the feed, the non-converted hydrocarbons, aliphatic monoalcohol and ether.

The effluent drawn off at the bottom through line 9 comprises a tertiary alkyl ether containing the lowest possible amount of monoalcohol(s).

A mixture of reactive and non-reactive hydrocarbons and of aliphatic monoalcohol(s) carried over by azeotropy is recovered through line 2 at the top of fractionating column F2.

The acid catalyst used in reactor R1, in the distillation-reaction zone and in reactor R2 is generally selected from all the catalysts known to the man skilled in the art to carry out the reaction considered. It can be selected for example from sulfuric acid, hydrofluoric acid, aluminum chloride, boron fluoride, carbonaceous, sulfonated matter, such as sulfonated carbon, sulfonated phenol-formaldehyde resins, sulfonated coumarone-indene polymers, or preferably sulfonated styrene-divinylbenzene copolymer resins. A zeolitic catalyst can also be used. It is also possible to use other compounds, notably mineral compounds, comprising sulfonic groups (for example sulfonated polysiloxanes).

Figure 4:
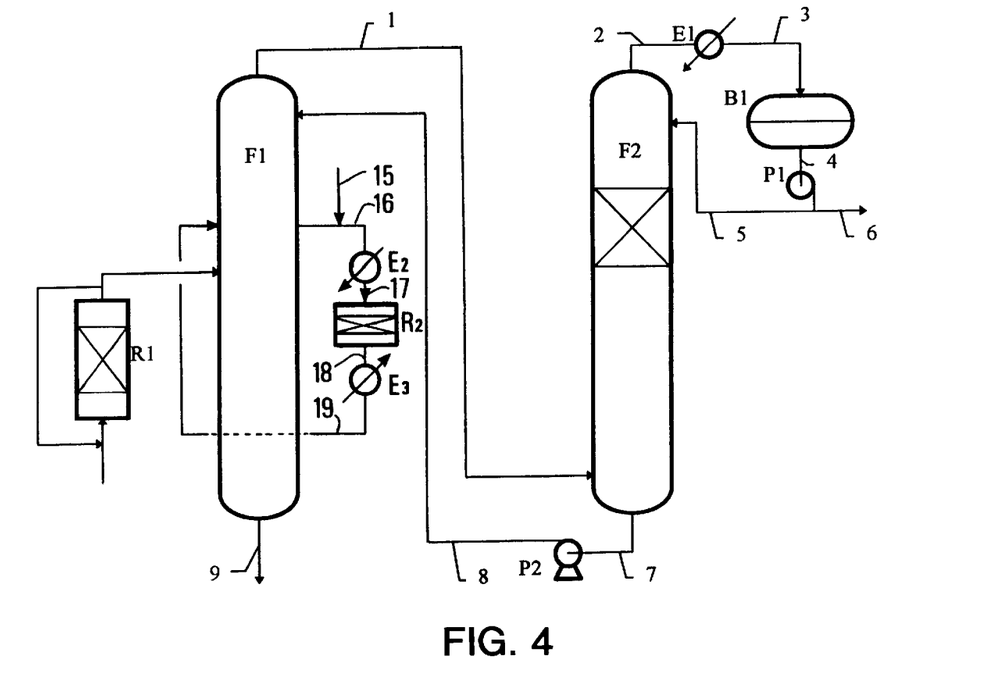
FIGS. 4–9 illustrate embodiments in accordance with the invention.

FIG. 4 diagrammatically shows an embodiment according to the invention of the process for preparing tertiary alkyl ether wherein the effluent of etherification reaction section R1 is fed into a fractionating column F1 where it is distilled, so as to produce at the bottom, through line 9, a tertiary alkyl ether containing the lowest possible amount of monoalcohol(s) and, at the top, through line 1, a mixture of hydrocarbons and of aliphatic monoalcohol carried along by azeotropy. This top product is fed into a distillation-reaction column F2. The bottom product of this distillation-reaction column F2 flowing out through line 7 is then sent through pump P2 and line 8 as reflux of fractionating column F1. In the embodiment of the process comprising a finishing reactor fed by drawing off liquid (line 16) from distillation column F1, the effluent of this reactor is re-injected substantially slightly below the draw-off level in column F1 (line 19). The feed of this finishing reactor R2 is mixed with a complementary amount of at least one aliphatic monoalcohol introduced through line 15. The temperature of this mixture is then adjusted in heat exchanger E2. The product leaving this exchanger is thereafter fed into reactor R2 through line 17. The effluent of this reactor is fed into heat exchanger E3 through line 18 in order to adjust its temperature. The effluent of this exchanger E3 is injected into the distillation-reaction column through line 19. A liquid product is generally drawn off above the feed point of the distillation zone.

Figure 5:
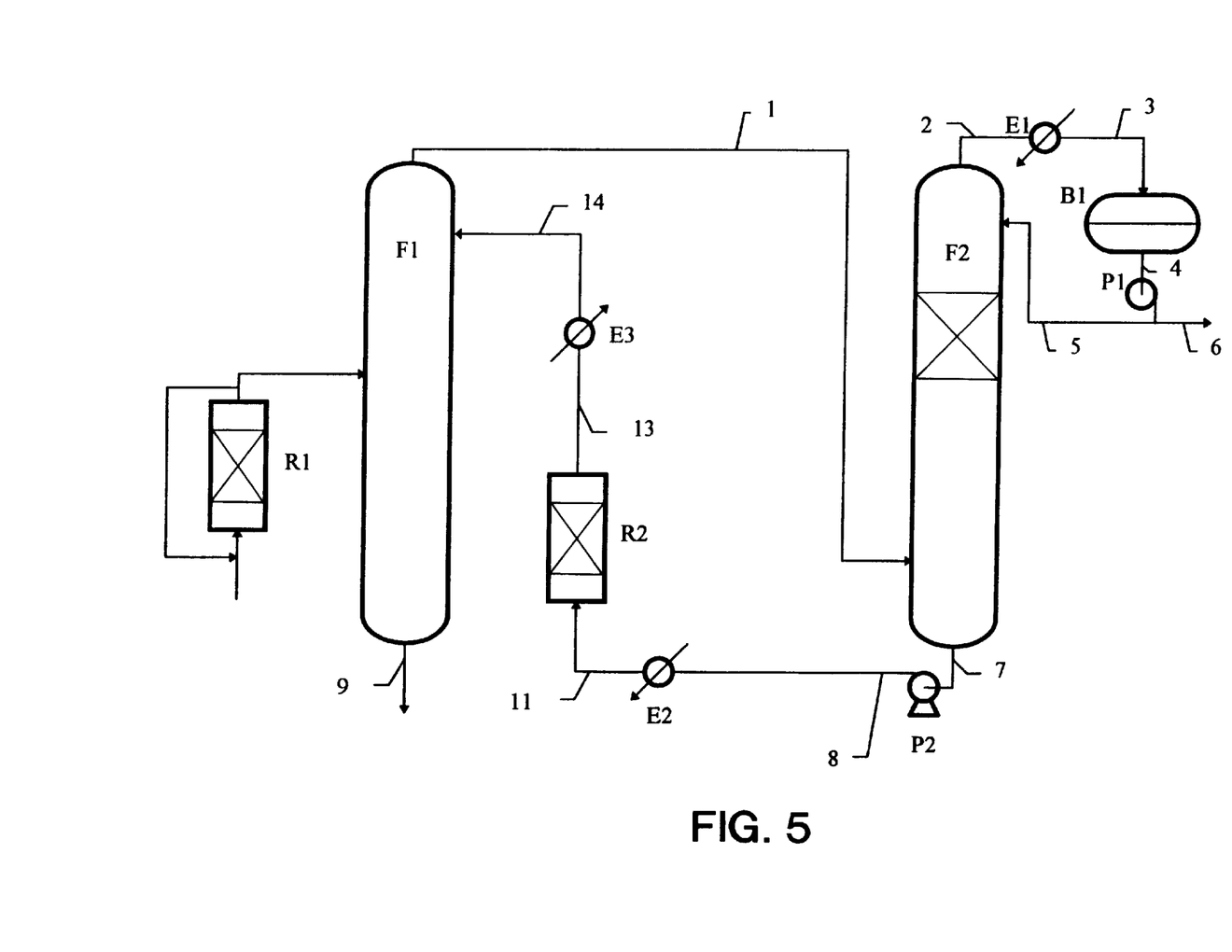

FIG. 5 diagrammatically shows another embodiment according to the invention of the process for preparing tertiary alkyl ether comprising a finishing reactor on the reflux device of fractionating column F1 and wherein the temperature of the feed of finishing reactor F2 is adjusted by means of heat exchanger E2 and the temperature of the effluent of this reactor R2 is also adjusted by means of heat exchanger E3. The product leaving pump P2 is thus fed into heat exchanger E2 through line 8 and the effluent leaving this heat exchanger E2 through line 11 is used as feed of finishing reactor R2, and the effluent leaving reactor R2 through line 13 is then fed into heat exchanger E3. The effluent flowing from this heat exchanger E3 through line 14 is then used as reflux of fractionating column F1. The other elements schematized in this figure are identical to those described in connection with the previous figures.

Figure 6:
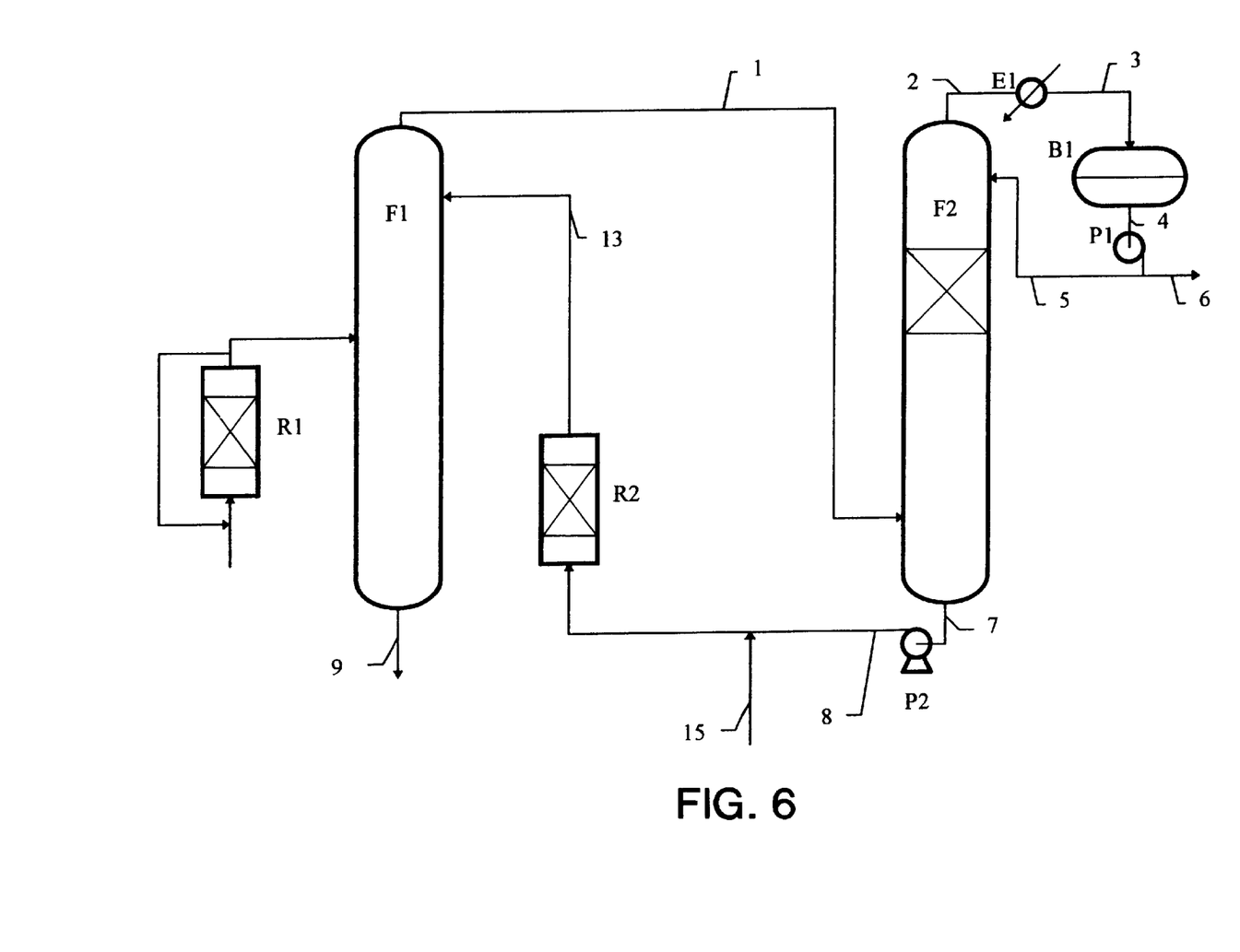

FIG. 6 diagrammatically shows another embodiment according to the invention of the process wherein a complementary amount of at least one aliphatic monoalcohol, which can be the same alcohol as the alcohol used in the main etherification reactor or a different monoalcohol, for example selected from methanol, ethanol, propanol and isopropanol, is injected through line 15 upstream from finishing reactor R2. The product leaving pump P2 through line 8 is thus mixed with an amount of at least one aliphatic monoalcohol from line 15, and the mixture is fed into finishing reactor F2. The effluent flowing from reactor R2 through line 13 is thereafter used as reflux of fractionating column F1. The other elements schematized in this figure are identical to those described in connection with the previous figures.

Figure 7:
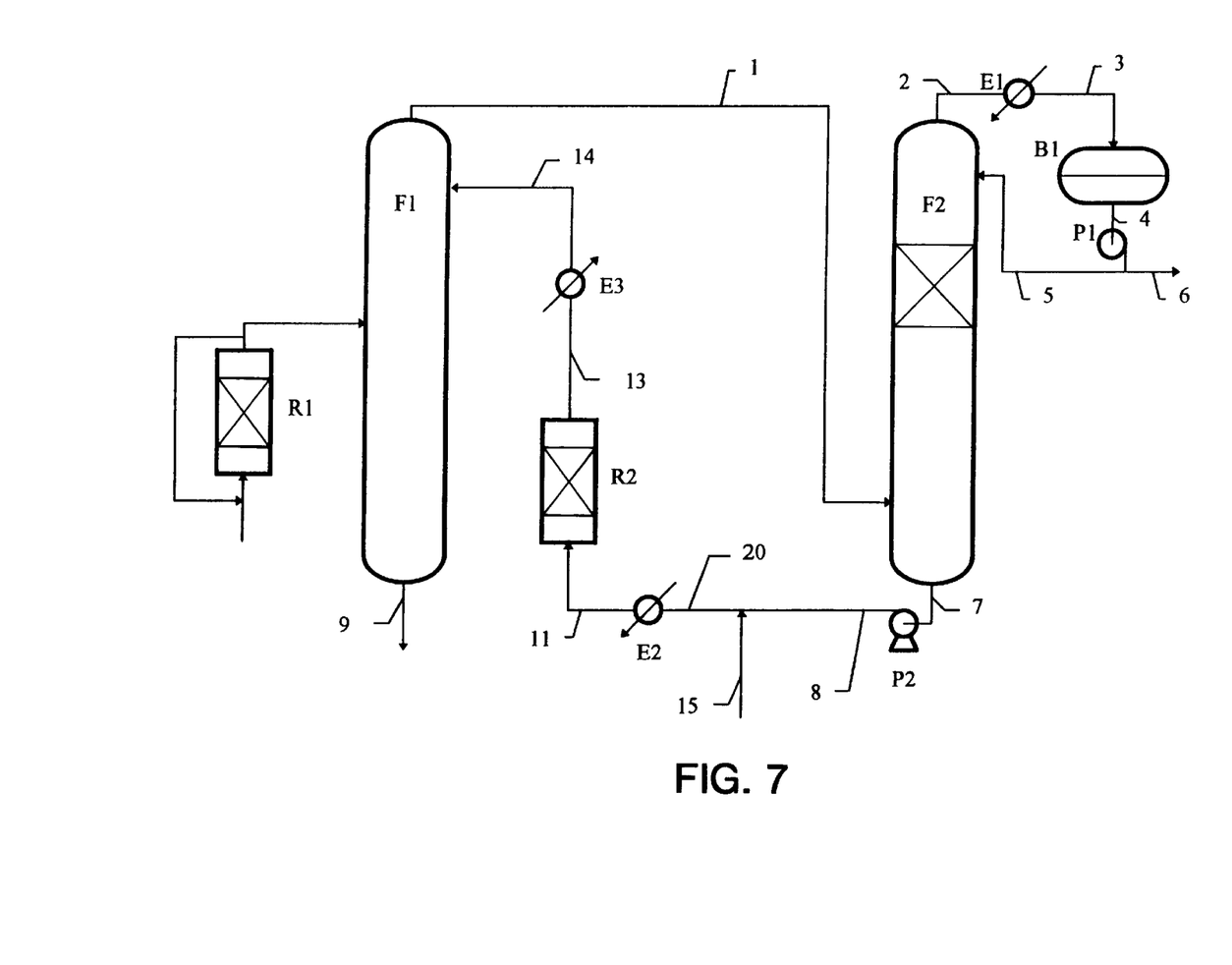

FIG. 7 diagrammatically shows another embodiment according to the invention of the process which combines the embodiments of FIGS. 5 and 6 insofar as a complementary amount of at least one aliphatic alcohol is added upstream from finishing reactor R2 through line 15 and the temperature of the feed and of the effluent of this reactor is adjusted. According to this embodiment, the product leaving pump P2 through line 8 is thus mixed with an amount of at least one aliphatic monoalcohol flowing in through line 15. This mixture is fed, through line 20, into heat exchanger E2. The effluent flowing from this heat exchanger E2 through line 11 is used as feed of finishing reactor R2. The effluent flowing out of reactor R2 through line 13 is then sent into heat exchanger E3. The effluent leaving this exchanger E3 through line 14 is then used as reflux of fractionating column F1. The other elements schematized in this figure are identical to those described in connection with the previous figures.

Figure 8:
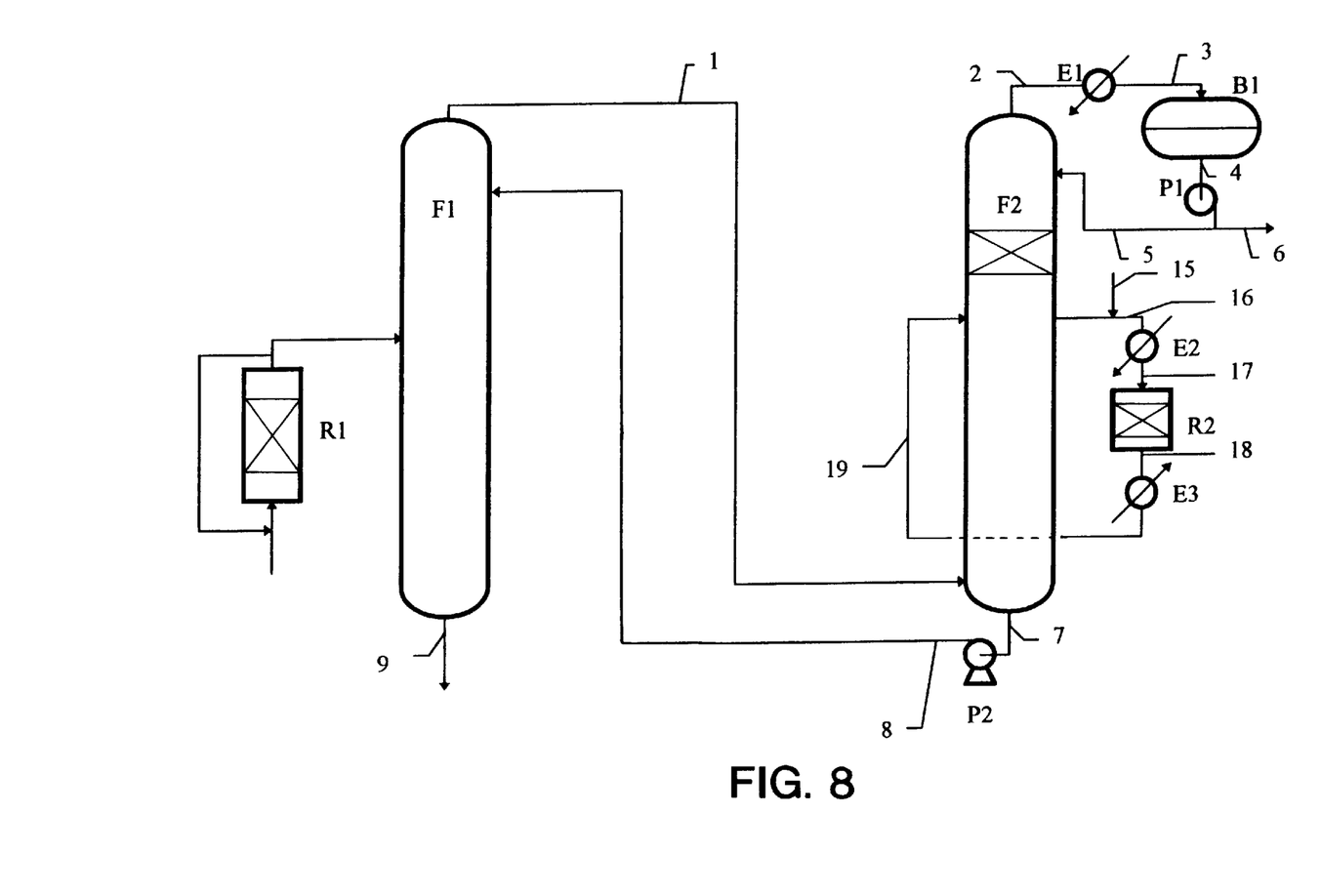

FIG. 8 shows another embodiment of the process comprising a finishing reactor fed by drawing off liquid from distillation-reaction column F2, the effluent of this reactor being re-injected substantially slightly below the draw-off level of column F2. The feed of this finishing reactor R2 (line 16) is mixed with a complementary amount of at least one aliphatic monoalcohol introduced through line 15. The temperature of this mixture is then adjusted in heat exchanger E2. The product leaving this exchanger is thereafter fed into reactor R2 through line 17. The effluent of this reactor is fed into heat exchanger E3 through line 18 in order to adjust the temperature thereof The effluent of exchanger E3 is injected into the distillation-reaction column through line 19.

Figure 9:
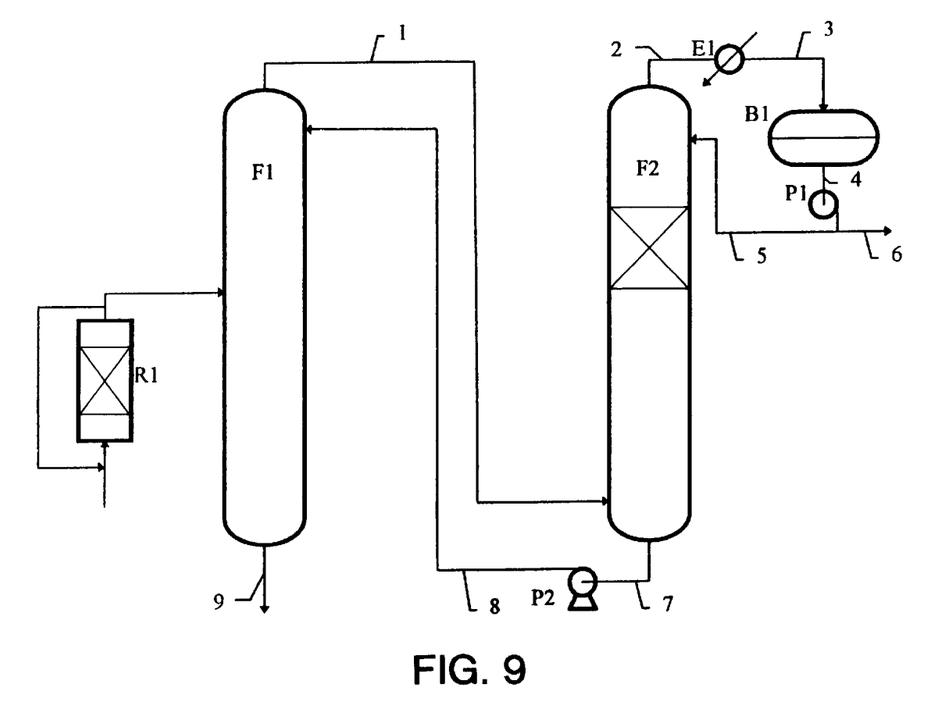

FIG. 9 diagrammatically shows an embodiment according to the invention of the process for preparing tertiary alkyl ether wherein the effluent of the etherification reaction section R1 is fed into a fractionating column F1 where it is distilled in order to produce, at the bottom, through line 9, a tertiary alkyl ether containing the lowest possible amount of monoalcohol(s) and, at the top, through line 1, a mixture of hydrocarbons and of aliphatic monoalcohol carried along by azeotropy. This top product is fed into a distillation-reaction column F2. The bottom product of this distillation-reaction column F2 flowing out through line 7 is then sent back through pump P2 and line 8 as reflux of fractionating column F1.

The following examples illustrate the invention. Examples 1, 2 and 3 are comparative examples.

EXAMPLES 1 TO 8

Ethyl tert-butyl ether (ETBE) was prepared on the one hand according to the conventional pattern (patterns 1, 2 and 3 in connection with FIGS. 1, 2 and 3 respectively) and on the other hand according to the embodiments described in the invention (patterns 4, 5, 6, 7, 8 and 9 in connection with FIGS. 4, 5, 6, 7, 8 and 9 respectively).

The following table shows the composition of the feed and the isobutene conversion in the main reaction section R1 and the operating conditions implemented for each pattern, in the finishing reactor when there is one, as well as the global conversion, the amount of ethanol obtained at the bottom of fractionating column F1 and at the top of distillation-reaction column F2.

Operating conditions in the finishing reactor:

Catalyst: acid resin (sulfonated styrene-divinylbenzene copolymer)

Reactor type: fixed bed

Phase: liquid

Pressure 7.8. $10^5$ Pa.

| Characteristics | FIG. 1 | FIG. 2 | FIG. 3 | FIG. 4 | FIG. 5 | FIG. 6 | FIG. 7 | FIG. 8 | FIG. 9 |
|---|---|---|---|---|---|---|---|---|---|
| Isobutene content in the feed entering reaction section R1 (% weight) | 22.9 | 22.9 | 22.9 | 22.9 | 22.9 | 22.9 | 22.9 | 22.9 | 22.9 |
| Isobutene conversion in reaction section R1 (%) | 92.3 | 92.3 | 92.3 | 92.3 | 92.3 | 92.3 | 92.3 | 92.3 | 92.3 |
| Number of reaction zones in distillation-reaction column F2 | 0 | 0 | 9 | 5 | 5 | 5 | 5 | 5 | 5 |
| Ethanol content in the raffinate of distillation-reaction column F2 (% by weight) | 1.5 | 1.4 | 0.47 | 1.0 | 0.6 | 0.9 | 1.0 | 1.0 | 0.47 |
| Ethanol content at the bottom of the fractionating column (F1 or F2 FIG. 3)(% by weight) | 3.5 | 3.5 | 3.5 | 3.5 | 3.5 | 3.5 | 3.5 | 3.5 | 3.5 |
| Ethanol/isobutene molar ratio at the inlet of reaction section R1 | 1.05 | 1.05 | 1.05 | 1.05 | 1.05 | 1.05 | 1.05 | 1.05 | 1.05 |
| Ethanol/isobutene molar ratio at the inlet of fractionating column F1 | 1.86 | 1.86 | 1.86 | 1.86 | 1.86 | 1.86 | 1.86 | 1.86 | 1.86 |
| Ethanol/isobutene molar ratio at the inlet of finishing reactor R2 | 0.8 | 2.0 | ** | 3.7 | 1.4 | 4.0 | 3.6 | 3.6 | ** |
| Ethanol/isobutene molar ratio for the whole reaction unit | 1.05 | 1.05 | 1.05 | 1.08 | 1.05 | 1.08 | 1.08 | 1.08 | 1.05 |
| Temperature at the inlet of finishing reactor R2 (° C.) | 57.2 | 68.6 | ** | 55 | 55 | 72.5 | 54.5 | 54.5 | ** |
| Temperature at the outlet of finishing reactor R2 (° C.) | 59.5 | 69.8 | ** | 56.3 | 56.6 | 73.5 | 56.3 | 56.2 | ** |
| Global isobutene conversion (%) | 94.50 | 94.60 | 97.40 | 97.85 | 97.50 | 97.70 | 97.90 | 97.91 | 97.41 |

** Absence of finishing reactor

Implementation of the process surprisingly allows to increase according to the invention the global isobutene conversion with a catalytic column containing less reaction zones in the embodiments of examples 4 to 9 (5 reaction zones instead of 9 reaction zones). Knowing that a reaction zone in a column occupies about 3 meters in height, the height of the distillation-reaction column can be decreased by about 12 meters, which represents a sizeable investment decrease.

Furthermore, the additional reaction section, when there is one, is outside the distillation column and can consequently be operated under optimum and independent temperature and pressure conditions, thus allowing to maximize isobutene conversion. This can be seen for example by comparing the results obtained in FIG. 7 and those obtained in FIG. 6.

What is claimed is:

1. A distillation and reaction device comprising:

a) a reaction section having at least one delivery means for introducing a feed, b) a distillation-reaction section comprising
a distillation zone having a feed means for introducing effluent from said reaction section, and at least one means for drawing off product from the bottom of said distillation zone, and
at least one distillation-reaction zone having at least one catalyst bed, said at least one distillation-reaction zone being distinct from said distillation zone, c) at least one means for circulation of effluent from said reaction section to said feed means of said distillation zone, d) means for circulating effluent from said distillation zone to said at least one distillation-reaction zone, e) means for passing fluid from the bottom of said at least one distillation-reaction zone to provide, at least partly, reflux to the top of said distillation zone, and f) said distillation-reaction section further comprises at least one complementary reaction zone having at least one catalyst bed, wherein means are provided for supplying said at least one complementary reaction zone with fluid from either said distillation zone or from said at least one distillation-reaction zone, and means are provided for delivering fluid from said at least one complementary reaction zone to said distillation zone or said at least one distillation-reaction zone.

2. A device as claimed in claim 1, wherein means (e) for passing fluid from said at least one distillation-reaction zone provides total reflux to said distillation zone.

3. A device as claimed in claim 1, wherein the means (d) for circulating effluent from said distillation zone to said at least one distillation-reaction zone circulates effluent from the top of said distillation zone to said at least one distillation-reaction zone.

4. A device according to claim 3, further comprising a reflux device comprising at least one draw-off means situated at the top of the at least one distillation-reaction zone, means for feeding at least one condensation zone, at least one means for circulation of part of the effluent from said at least one condensation zone to the top of the at least one distillation-reaction zone, and at least one means for drawing off another part of the effluent of said at least one condensation zone.

5. A device as claimed in claim 4, wherein the at least one complementary reaction zone is situated on the means (e) for passing fluid from the bottom of said at least one distillation-reaction zone to the top of said distillation zone as reflux.

6. A device as claimed in claim 4, wherein the means for supplying fluid to said at least one complementary reaction zone comprises at least one temperature control means.

7. A device as claim in claim 4, wherein the means for delivering fluid from said at least one complementary reaction zone comprises at least one temperature control means.

8. A device as claimed in claim 4, wherein the at least one complementary reaction zone comprises at least one additional reactant(s) delivery means.

9. A device as claimed in claim 1, wherein the at least one distillation-reaction zone further comprises at least one reflux device.

10. A device as claimed in claim 9, wherein said reflux device comprises at least one draw-off means situated at the top of the at least one distillation-reaction zone, and wherein said reflux device further comprises means for feeding at least one condensation zone, at least one means for circulation of part of the effluent from said at least one condensation zone to the top of the at least one distillation-reaction zone and at least one means for drawing off another part of the effluent of said at least one condensation zone.

11. A device as claimed in claim 1, wherein the at least one complementary reaction zone is situated on the means (e) for passing fluid from the bottom of said at least one distillation-reaction zone to the top of said distillation zone as reflux.

12. A device as claimed in claim 1, wherein the means for supplying fluid to said at least one complementary reaction zone comprises at least one temperature control.

13. A device as claimed in claim 1, wherein the means for delivering fluid from said at least one complementary reaction zone to said distillation zone comprises at least one temperature control.

14. A device as claimed in claim 1, wherein the at least one complementary reaction zone further comprises at least one additional reactant(s) delivery means.

15. A device as claimed in claim 1, wherein the at least one complementary reaction zone is connected on the one hand to said distillation zone, at the height of a draw-off level, by the means for supplying fluid, and further connected on the other hand to said distillation zone in proximity to said draw-off level by a means for circulation of the effluent of said at least one complementary reaction zone.

16. A device as claimed in claim 1, wherein the at least one complementary reaction zone is connected to said distillation zone at the height of a draw-off level, by the means for supplying fluid and further connected to said distillation zone substantially at the height of said draw-off level by a means for circulation of the effluent of said at least one complementary reaction zone.

17. A device as claim in claim 16, wherein the draw-off level is situated between said feed means of said distillation zone and the top of said distillation zone.

18. A device as claimed in claim 1, wherein the at least one complementary reaction zone is connected on the one hand to said distillation-reaction zone, at the height of a draw-off level, by the means for supplying fluid and further connected on the other hand to said distillation-reaction zone in proximity to said draw-off level by a means for circulation of the effluent of said at least one complementary reaction zone.

19. A device as claimed in claim 18, wherein the draw-off level is situated between the bottom of the distillation-reaction zone and the bottom of the catalyst bed situated in the lowest part of said at least one distillation-reaction zone.

20. A device comprising:
a) a reaction section,
b) a distillation-reaction section comprising a distillation zone having a feed means, and at least one distillation-reaction zone having at least one catalyst bed, said at least one distillation-reaction zone being distinct from said distillation zone,
c) at least one means for circulation of effluent from said reaction section to said distillation zone, and
d) means for circulating effluent from said distillation zone to said at least one distillation-reaction zone,
e) means for passing liquid from the bottom of said distillation-reaction zone so as to provide, at least partly, reflux to the top of said distillation zone,
wherein said distillation-reaction section further comprises at least one complementary reaction zone, comprising feed means and at least one catalyst bed, wherein the at least one complementary reaction zone is connected by said feed means to said distillation zone, at the height of a draw-off level, and further connected to said distillation zone in proximity to said draw-off level by a means for circulation of effluent of said at least one complementary reaction zone.

21. A device as claimed in claim 20, wherein the at least one complementary reaction zone is connected to said distillation zone substantially at the height of said draw-off level by said means for circulation of effluent of said at least one complementary reaction zone.

22. A device as claimed in claim 21, wherein the draw-off level is situated between the feed means point of the distillation zone and the top of said distillation zone.

23. A device comprising:
a) a reaction section,
b) a distillation-reaction section comprising a distillation zone having a feed means, and at least one distillation-reaction zone having at least one catalyst bed, said at least one distillation-reaction zone being distinct from said distillation zone,
c) at least one means for circulation of effluent from said reaction section to said distillation zone, and
d) means for circulating effluent from said distillation zone to said at least one distillation-reaction zone,
e) means for passing liquid from the bottom of said at least one distillation-reaction zone so as to provide, at least partly, reflux to the top of said distillation zone, wherein said distillation-reaction section further comprises at least one complementary reaction zone, comprising feed means and at least one catalyst bed, wherein the at least one complementary reaction zone is connected by said feed means to said distillation-reaction zone, at the height of a draw-off level, and further connected to said distillation-reaction zone in proximity to said draw-off level by a means for circulation of effluent of said at least one complementary reaction zone.

24. A device as claimed in claim 23, wherein the draw-off level is situated between the bottom of the at least one distillation-reaction zone and the bottom of the at least one catalyst bed situated in the lowest part of said at least one distillation-reaction zone.

* * * * *